(12) United States Patent
Vangara et al.

(10) Patent No.: US 11,361,673 B2
(45) Date of Patent: Jun. 14, 2022

(54) DIET MANAGEMENT APPARATUS

(71) Applicant: Rajesh Vangara, Concord, NC (US)

(72) Inventors: Ravi Chandar Vangara, Bangalore (IN); Vipin Vangara, Charlotte, NC (US); Siddharth Vangara, Concord, NC (US)

(73) Assignee: Rajesh Vangara

( * ) Notice: Subject to any disclaimer, the term of this patent is extended or adjusted under 35 U.S.C. 154(b) by 540 days.

(21) Appl. No.: 16/555,105

(22) Filed: Aug. 29, 2019

(65) Prior Publication Data

US 2021/0065579 A1 Mar. 4, 2021

(51) Int. Cl.
| | |
|---|---|
| *G09B 19/00* | (2006.01) |
| *G01G 19/414* | (2006.01) |
| *G01N 33/02* | (2006.01) |
| *G01N 21/27* | (2006.01) |
| *G06T 7/40* | (2017.01) |
| *G06K 9/62* | (2022.01) |
| *G06T 7/90* | (2017.01) |
| *G06V 20/68* | (2022.01) |

(52) U.S. Cl.
CPC ..... *G09B 19/0092* (2013.01); *G01G 19/4146* (2013.01); *G01N 21/27* (2013.01); *G01N 33/02* (2013.01); *G06K 9/6267* (2013.01); *G06T 7/40* (2013.01); *G06T 7/90* (2017.01); *G06T 2207/10012* (2013.01); *G06T 2207/10024* (2013.01); *G06V 20/68* (2022.01)

(58) Field of Classification Search
CPC ........... G09B 19/0092; G01G 19/4146; G01N 21/27; G01N 33/02; G06K 9/6267; G06T 7/40; G06T 7/90; G06T 2207/10012; G06T 2207/10024; G06V 20/68; G06V 20/52; G06Q 50/10
USPC ....................................................... 434/127
See application file for complete search history.

(56) References Cited

U.S. PATENT DOCUMENTS

| | | | |
|---|---|---|---|
| 8,330,057 B2 | 12/2012 | Sharawi et al. | |
| 9,146,147 B1 * | 9/2015 | Bakhsh | .................. A47G 21/02 |
| 9,364,106 B1 | 6/2016 | Ortiz | |
| 2013/0025944 A1 * | 1/2013 | Batsikouras | ....... G01G 19/4146 |
| | | | 177/25.13 |
| 2013/0029298 A1 * | 1/2013 | Batsikouras | ....... G01G 19/4146 |
| | | | 434/127 |

(Continued)

*Primary Examiner* — Ali Bayat
(74) *Attorney, Agent, or Firm* — Jason C. Cameron

(57) ABSTRACT

A diet management apparatus. The apparatus includes a weighing unit including weighing scales and food trays which includes one or more slots to receive corresponding food substances. The weighing scales are configured to calculate weight of food substances corresponding to each slot. The apparatus includes an image acquisition device to capture images of the one or more food substances the one or more slots. The apparatus includes a control unit configured to analyse the captured images to identify a category of each of the one or more food substances, comparing the calculated weight corresponding to identified category of each food substances with a predefined weight and determine calorie count GI/GL count of each food substances based on a compared result. The apparatus includes audio alerts based on food caloric values; GI/GL recommended by health care provider. The apparatus is configured to communicate with the end user computing device.

18 Claims, 2 Drawing Sheets

(56) References Cited

U.S. PATENT DOCUMENTS

| | | | |
|---|---|---|---|
| 2016/0035248 A1* | 2/2016 | Gibbs | G06T 7/60 |
| | | | 434/127 |
| 2016/0192446 A1* | 6/2016 | Seddik | H05B 6/6447 |
| | | | 219/705 |
| 2016/0252390 A1 | 9/2016 | Batsikouras | |
| 2017/0035249 A1* | 2/2017 | Dickson, Jr. | A47J 43/04 |
| 2017/0124912 A1* | 5/2017 | Ashby | G09B 19/0092 |
| 2018/0335336 A1* | 11/2018 | Gyi | G01G 19/4146 |

* cited by examiner

DIET MANAGEMENT APPARATUS

BACKGROUND

Embodiments of a present disclosure relate to a Multi-scale weighing system and more particularly to a digital diet management apparatus.

Dieting is the practice of eating food in a regulated fashion to achieve or maintain a controlled weight. Poor diets, such as overeating, under eating or consuming poor-quality food have direct correlations to certain medical conditions such as diabetes, heart disease, hypertension, chronic kidney disease, obesity, and the like. For consumers and patients trying to control the quality/quantity and habit of consuming food, it is often difficult to identify what kinds of food and eating habits may improve their health condition. It is cumbersome for them to meet their prescribed nutritional requirements or dietary regimen necessary each time they prepare or consume a meal. Person's participating in dieting programs often utilize various types of measuring apparatus to measure the diet related parameters.

Traditionally, while executing the dieting programs the individual often use a weight scale, pencil, paper and/or calculator for tracking progress associated with dieting. The caloric and nutritional information associated with foods for dieting may be retrieved from a book or other reference source. However, the traditional approaches are cumbersome and lead to error in calculations, as the traditional process does not analyse the data over a period of time.

Currently available diet tracking approaches utilize food scales which are difficult to use and are oftentimes only capable of weighing a single item at a time. Even advanced food scales are incapable of weighing multiple items simultaneously and unable to provide caloric value, Glycaemic index and glycaemic load, independent analysis of the different food items being weighed.

Furthermore, with the advancement in technology the food scales have been developed that allow multiple food items to be weighed simultaneously. In order to achieve that, they use multiple plates or a single partitioned container. However, such food scales are incapable of differentiating between the different types of food, and unable to provide accurate analysis for Glycaemic Load (GL) and Glycaemic Index (GI) of the food, type of the diet and weight of the food a person should take, based on health care practitioner and or a dietician recommendation.

Hence, there is a need for an improved diet management system to address the aforementioned issue(s).

BRIEF DESCRIPTION

In accordance with an embodiment of the present disclosure, a diet management apparatus is provided. The apparatus includes a weighing unit. The weighing unit includes one or more weighing scales operatively coupled to a stand. The weighing unit also includes corresponding one or more food trays operatively coupled to the one or more weighing scales. The one or more food trays includes corresponding one or more slots and configured to receive corresponding one or more food substances. The one or more weighing scales are configured to calculate weight of each of the one or more food substances corresponding to each of the one or more slots. The one or more weighing scales are also configured to calculate aggregate weight of the one or more food substances in the corresponding one or more food trays. The apparatus also includes an image acquisition device operatively coupled to the stand. The image acquisition device is configured to capture one or more images of the one or more food substances in the each of the one or more slots of the one or more food trays. The apparatus further includes a control unit operatively coupled to the weighing unit and the image acquisition device. The control unit is configured to receive calculated weight of each of the one or more food substances corresponding to each of the one or more slots, calculated aggregate weight of the one or more food substances in the one or more food trays and one or more captured images. The control unit is also configured to analyse the one or more captured images to identify a category of each of the one or more food substances. The control unit is further configured to compare the calculated weight corresponding to identified category of each of the one or more food substances with a predefined weight corresponding to identified category of each of the one or more food substances. The control unit is further configured to determine a calorie count, a Glycaemic index and a Glycaemic load count of each of the one or more food substances corresponding to each of the one or more slots based on a compared result. The apparatus is configured to interface with the end user computing devices to update the amount of caloric food consumed by the outpatient against the recommendations of the dietician or health care practitioner. The food consumption pattern is data and pattern are monitored by the health care practitioner.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

DETAILED DESCRIPTION

Figure 1:
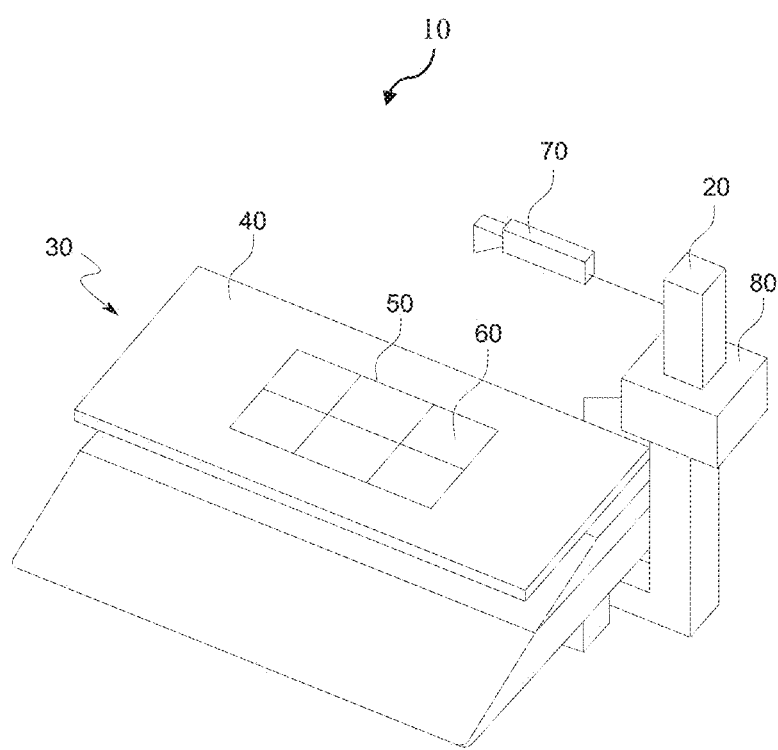
FIG. 1 is a schematic representation of a diet management apparatus in accordance with an embodiment of the present disclosure.

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure.

The terms "comprises", "comprising", or any other variations thereof, are intended to cover a non-exclusive inclusion, such that a process or method that comprises a list of steps does not include only those steps but may include other steps not expressly listed or inherent to such a process or method. Similarly, one or more devices or sub-systems or elements or structures or components preceded by "comprises . . . a" does not, without more constraints, preclude the existence of other devices, sub-systems, elements, structures, components, additional devices, additional sub-systems, additional elements, additional structures or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

Embodiments of the present disclosure relate to a diet management apparatus. The apparatus includes a weighing unit. The weighing unit includes a one or more weighing scale operatively coupled to a stand. The weighing unit also includes corresponding one or more food trays operatively coupled to the one or more weighing scale. The one or more food trays includes corresponding one or more slots and configured to receive corresponding one or more food substances. The one or more weighing scales are configured to calculate weight of each of the one or more food substances corresponding to each of the one or more slots. The one or more weighing scales are also configured to calculate aggregate weight of the one or more food substances in the one or more food trays. The apparatus also includes an image acquisition device operatively coupled to the stand. The image acquisition device is configured to capture one or more images of the one or more food substances in the each of the one or more slots of the one or more food trays. The apparatus further includes a control unit operatively coupled to the weighing unit and the image acquisition device. The control unit is configured to receive calculated weight of each of the one or more food substances corresponding to each of the one or more slots, calculated aggregate weight of the one or more food substances in the one or more slots of the one or more food trays and one or more captured images. The control unit is also configured to analyse the one or more captured images to identify a category of each of the one or more food substances. The control unit is further configured to compare the calculated weight corresponding to identified category of each of the one or more food substances with a predefined weight corresponding to identified category of each of the one or more food substances. The control unit is further configured to determine a calorie count, a Glycaemic index and a Glycaemic load count of each of the one or more food substances corresponding to each of the one or more slots based on a compared result.

FIG. 1 is a schematic representation of a diet management apparatus 10 in accordance with an embodiment of the present disclosure. The apparatus 10 includes a stand 20. In one embodiment, the stand 20 may be a collapsible stand. The apparatus 10 also includes a weighing unit 30. The weighing unit 30 includes one or more weighing scales 40 operatively coupled to a first end of the stand 20. The weighing unit 30 also includes one or more food trays 50 operatively coupled to the one or more weighing scales 40. The one or more food trays 50 includes corresponding one or more slots 60. The one or more slots 60 are configured to receive corresponding one or more food substances. In one embodiment, the one or more slots 60 of the corresponding one or more food trays 50 may include a corresponding barcode or a corresponding number.

The weighing scale 40 is configured to calculate weight of each of the one or more food substances corresponding to each of the one or more slots 60. The weighing scale 40 is also configured to calculate aggregate weight of the one or more food substances. In some embodiments the one or more weighing scale 40 may include one or more weight sensors (not shown in FIG. 1) operatively coupled to each of the one or more slots 60. In such embodiment, one or more weight sensors contemplated herein may measure weight of the one or more food substances in various ways which may include, but are not limited to, electrically resistive strain gauges, force sensitive resistors, photoelectric weight sensors, hydraulic weight sensors, pneumatic weight sensors, and the like. The one or more weight sensors may be configured to calculate weight of each of the one or more food substances corresponding to each of the one or more slots. In a specific embodiment, the weighing unit 30 may include a scale which may also be configured to calculate small quantity of weight of the one or more food substances ranging from 1 gram to 20 gram of weight suitable to measure salt, sugar, spices, pepper (Red and black) and the like.

Furthermore, the apparatus 10 includes an image acquisition device 70 operatively coupled to a second end of the stand 20. The image acquisition device 70 is configured to capture one or more images of the one or more food substances in the each of the one or more slots 60. In one embodiment, the image acquisition device 70 may include a three-dimensional camera.

Moreover, the apparatus 10 also includes a control unit 80 operatively coupled to the weighing unit 30 and the image acquisition device 70. In one embodiment, the control unit 80 may be configured to receive an activation signal from an external computing device (not shown in FIG. 1). In such embodiment, the external computing device may include a computer, a laptop, a cellular phone, a personal digital assistant, a tablet, a cloud server and the like. Upon receiving the activation signal, the control unit 80 is configured to receive calculated weight of each of the one or more food substances corresponding to each of the one or more slots 60, calculated aggregate weight of the one or more food substances in the food tray 50 and one or more captured images. In some embodiments, the control unit 80 may be configured to receive one or more information associated with the one or more food substances from a user via a natural language voice command. In a specific embodiment, when the one or more food substances are not identifiable by the image acquisition device 70, the apparatus 10 may enable the user to select the one or more food substances from a database (not shown in FIG. 1) of the external computing device.

The control unit 80 is also configured to analyse the one or more captured images to identify a category of each of the one or more food substances. In one embodiment, the control unit 80 may be configured to identify colour and texture of the one or more food substances corresponding to the one or more slots 60 of the food tray 50. In such embodiment, the category may correspondences to colour, texture and the like.

Subsequently, the control unit 80 is further configured to compare the calculated weight corresponding to identified category of each of the one or more food substances with a predefined weight corresponding to identified category of each of the one or more food substances. The control unit 80 is further configured to determine a calorie count, a Glycaemic index and a Glycaemic load count of each of the one or more food substances corresponding to each of the one or more slots 60 based on a compared result. In one embodiment, the control unit 80 may also be configured to determine aggregate calorie count, aggregate nutrition count, aggregate Glycaemic index and aggregate Glycaemic load of the one or more food substances in the one or more food trays 50.

Figure 2:
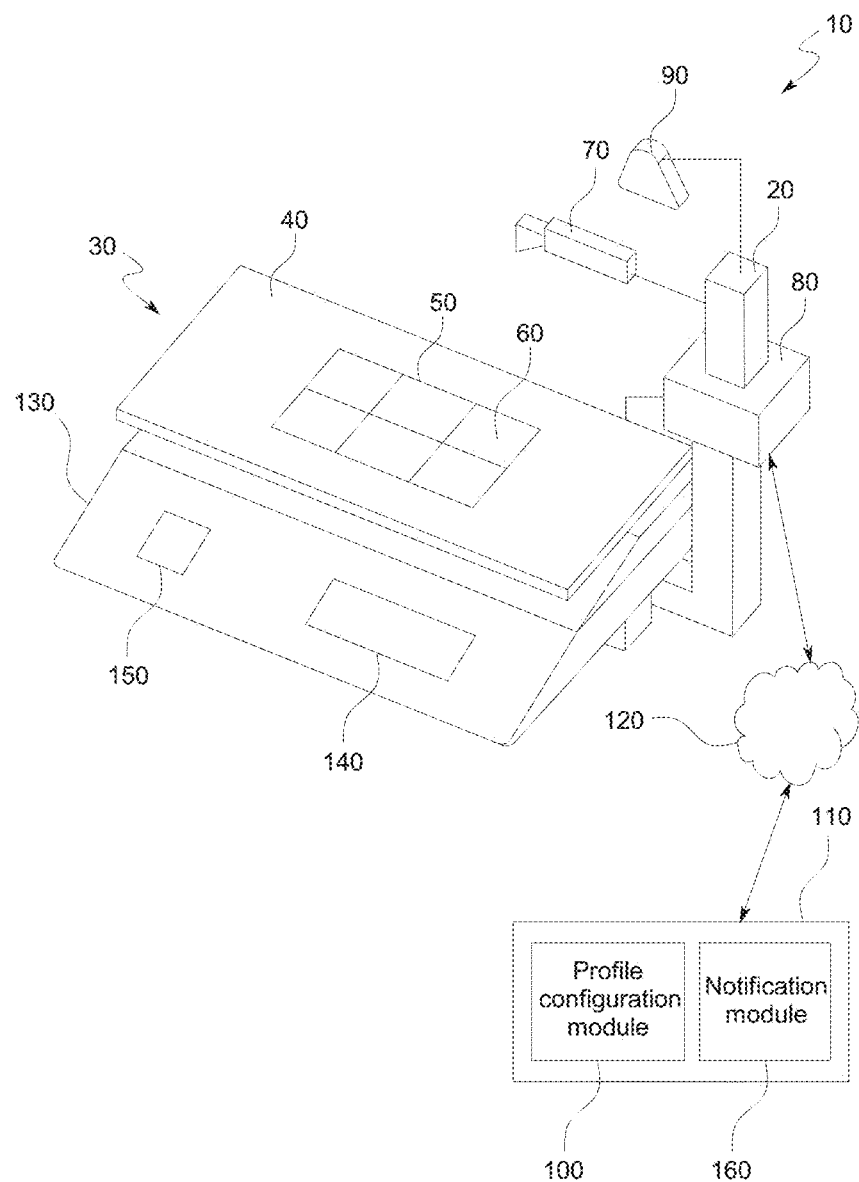
FIG. 2 is a schematic representation of one embodiment of the diet management apparatus of FIG. 1 in accordance with an embodiment of the present disclosure; and Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

FIG. 2 is a schematic representation of one embodiment of the diet management apparatus 10 of FIG. 1 in accordance with an embodiment of the present disclosure. The apparatus 10 includes a weighing unit 30. The weighing unit 30 includes a weighing scale 40 operatively coupled to a stand 20. The weighing unit 30 also includes a food tray 50 operatively coupled to the weighing scale 40. The food tray 50 includes one or more slots 60 and configured to receive corresponding one or more food substances. The weighing scale 40 is configured to calculate weight of each of the one or more food substances corresponding to each of the one or more slots 60. The weighing scale 40 is also configured to calculate aggregate weight of the one or more food substances in the food tray 50.

The apparatus 10 also includes an image acquisition device 70 operatively coupled to a second end of the stand 20. The image acquisition device is configured to capture one or more images of the one or more food substances in the each of the one or more slots 60 of the food tray 50. In one embodiment, the apparatus 10 may include an illumination device 90 operatively coupled to the second end of the stand 20. The illumination device 90 may be configured to provide illumination to the food tray 50.

Furthermore, the apparatus 10 further includes a control unit 80 operatively coupled to the weighing unit 30 and the image acquisition device 70. In one embodiment, the control unit 80 may be communicatively coupled to a profile configuration module 100. In such embodiment, the profile configuration module may be located in an external computing device 110 and communicate to the control unit 80 via a communication network 120. In such embodiment, the communication network 120 may include a wired communication medium such as local area network (LAN). In another embodiment, the communication network 120 may include a wireless communication medium such as radio frequency (RF) communication, Bluetooth, Infrared (IR) communication, wireless fidelity (wi-fi) or the like.

The profile configuration module 100 is configured to send an activation signal to the control unit 80 for activation of the weighing unit 30. In one embodiment, the profile configuration module 100 may be configured to store a diet plan of a user recommended by a healthcare provider. In some embodiments, the profile configuration module 100 may also be configured to store a medical profile of the user such as diabetic profile, blood pressure profile, cardiac profile, gastric profile and the like. Based on the stored information, the profile configuration module 100 may be configured to generate a diet profile of the user based on a recommended diet plan and the medical profile of the user.

In a specific embodiment, the profile configuration module 100 may also be configured to generate profile of one or more family members of the user. In one embodiment, the profile configuration module 100 may be configured to receive user preferences corresponding to requirement of caloric value or nutrition intake, such as low carb, high fat, high fibre and the like.

Moreover, the control unit 80 is configured to receive calculated weight of each of the one or more food substances corresponding to each of the one or more slots 60, calculated aggregate weight of the one or more food substances in the food tray 50 and one or more captured images. The control unit 80 is also configured to analyse the one or more captured images to identify a category of each of the one or more food substances. In one embodiment, the control unit 80 may be configured to identify colour and texture of the one or more food substances corresponding to the one or more slots 60 of the food tray 50. In such embodiment, the category may correspondences to colour, texture and the like.

Based on the received profile and identified category, the control unit 80 is further configured to compare the calculated weight corresponding to identified category of each of the one or more food substances with a predefined weight corresponding to identified category of each of the one or more food substances. The control unit 80 is further configured to determine a calorie count, a Glycaemic index and a Glycaemic load count of each of the one or more food substances corresponding to each of the one or more slots 60 based on a compared result. In one embodiment, the control unit 80 is configured to determine aggregate calorie count, aggregate nutrition count, aggregate Glycaemic index and aggregate Glycaemic load of the one or more food substances in the food tray 50. In a preferred embodiment, the control unit 80 may be configured to determine whether the one or more identified food substances, caloric value or nutrition intake is suitable for diet recommended by the healthcare provider. In such embodiment, the healthcare provider may include, a doctor, a nurse, a dietician or the like.

In some embodiments, the apparatus 10 may include an interface unit 130 operatively coupled to the weighing unit 30 and the control unit 80, wherein the interface unit 130 includes a display panel 140 and an input interface 150. In such embodiment, the display panel 140 may be configured to display the calculated weight of each of the one or more food substances corresponding to each of the one or more slots. In one embodiment, the display panel 140 may also be configured to display calculated aggregate weight of the one or more food substances in the food tray 50. In some embodiment, the display panel 140 may be further configured to display the calorie count, the nutrition count, the Glycaemic index and the Glycaemic load count of each of the one or more food substances corresponding to each of the one or more slots 60. In a specific embodiment, the display panel 140 may be configured to display the aggregate calorie count, the aggregate nutrition count, the aggregate Glycaemic index and the aggregate Glycaemic load of the one or more food substances in the food tray 50.

Subsequently, in one embodiment, the input interface 150 may be configured to receive selection of a number of the one or more slots 60 for weight calculation. In some embodiments, the input interface 150 may also be configured to enable the user to input a predetermined calorie count, nutrition count, Glycaemic index and Glycaemic load count as a reference value. In one embodiment, the apparatus 10 may further include a notification module 160 operatively coupled to the control unit 80. The notification module 160 is configured to generate one or more alerts. In such embodiment, the one or more alerts may include at least one of a diet recommendation alert and an alert of the calorie count, the nutrition count, the Glycaemic index and the Glycaemic load count. In a specific embodiment, the one or more alerts may include a visual alert or an audio alert. In such embodiment, the notification module 160 may transmit the one or more alerts to the external computing device 110 via the communication network 120. Further, the control unit 80 is configured to control the apparatus 10 via the external computing device 110, based on user preferences and one or more predefined configurations. In one embodiment, the apparatus includes audio alerts based on food caloric values; GI/GL recommended by health care provider.

Various embodiments of the diet management apparatus described above enables an electronic personal trainer to track the user's goals and help them achieve their target. Also, the apparatus is used to set a dieting plan and guidance based on input (verbal or textual) goals and calculated weight of the one or more food substances in the each of the one or more slots of the food tray.

In addition, the apparatus helps to determine a calorie count, a Glycaemic index and a Glycaemic load count of each of the one or more food substances which further guide the patient on the caloric value of the food that is going to be consumed and advises the patient to increase or reduce the quantity that could increase their glucose levels in blood.

Moreover, based on the visual analysis and weight the one or more food substances determines whether the food is suitable for example: Ketogenic diet or not. The apparatus provides opportunity to benchmark the global diet practices and success stories by the patients, healthcare providers and dieticians. The apparatus has an interface with external computing device configured to retrieve the caloric food consumed by the patient and day to day diet habits against the dietician or healthcare provider's recommendations.

It will be understood by those skilled in the art that the foregoing general description and the following detailed description are exemplary and explanatory of the disclosure and are not intended to be restrictive thereof.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

We claim:

1. A diet management apparatus comprising:
a weighing unit comprising:
one or more weighing scales operatively coupled to a stand;
one or more food trays operatively coupled to the corresponding one or more weighing scales, wherein the one or more food trays comprises corresponding one or more slots and configured to receive corresponding one or more food substances;
wherein the one or more weighing scales are configured to:
calculate weight of each of the one or more food substances corresponding to each of the one or more slots;
calculate aggregate weight of the one or more food substances in the one or more food trays;
an image acquisition device operatively coupled to the stand, wherein the image acquisition device is configured to capture one or more images of the one or more food substances in the each of the one or more slots;
a control unit operatively coupled to the weighing unit and the image acquisition device, wherein the control unit is configured to:
receive calculated weight of each of the one or more food substances corresponding to each of the one or more slots, calculated aggregate weight of the one or more food substances in the one or more food trays and one or more captured images;
analyse the one or more captured images to identify a category of each of the one or more food substances;
compare the calculated weight corresponding to identified category of each of the one or more food substances with a predefined weight corresponding to identified category of each of the one or more food substances; and
determine a calorie count, a Glycaemic index and a Glycaemic load count of each of the one or more food substances corresponding to each of the one or more slots based on a compared result.

2. The apparatus of claim 1, wherein the one or more weighing scales comprises corresponding one or more weight sensors operatively coupled to each of the one or more slots of the food tray.

3. The apparatus of claim 1, wherein the one or more weighing scales are configured to calculate weight of the one or more food substances ranging from 1 gram to 20 gram of weight.

4. The apparatus of claim 1, wherein the one or more slots comprises a corresponding barcode or a corresponding number.

5. The apparatus of claim 1, wherein the image acquisition device comprises a three-dimensional camera.

6. The apparatus of claim 1, wherein the control unit is communicatively coupled to a profile configuration module and configured to send an activation signal to the control unit.

7. The apparatus of claim 6, wherein the profile configuration module is configured to:
store a diet plan of a user recommended by a healthcare provider; and
store a medical profile of the user.

8. The apparatus of claim 7, wherein the profile configuration module is configured to generate a diet profile of the user based on a recommended diet plan and the medical profile of the user.

9. The apparatus of claim 1, wherein the control unit is configured to identify colour and texture of the one or more food substances corresponding to the one or more slots of the food tray based on the one or more captured images, through an image acquisition device.

10. The apparatus of claim 1, wherein the control unit is configured to determine aggregate calorie count, aggregate nutrition count, aggregate Glycaemic index and aggregate Glycaemic load of the one or more food substances in the food tray.

11. The apparatus of claim 1, further comprising an interface unit operatively coupled to the weighing unit and the control unit, wherein the interface unit comprises a display panel and an input interface.

12. The apparatus of claim 11, wherein the display panel is configured to:
- display the calculated weight of each of the one or more food substances corresponding to each of the one or more slots; and
- display calculated aggregate weight of the one or more food substances in the food tray.

13. The apparatus of claim 11, wherein the display panel is configured to:
- display the calorie count, the nutrition count, the Glycaemic index and the Glycaemic load count of each of the one or more food substances corresponding to each of the one or more slots; and
- display the aggregate calorie count, the aggregate nutrition count, the aggregate Glycaemic index and the aggregate Glycaemic load of the one or more food substances in the food tray.

14. The apparatus of claim 11, wherein the input interface is configured to receive selection of a number of the one or more slots for weight calculation.

15. The apparatus of claim 11, wherein the input interface is configured to enable the user to input a predetermined calorie count, nutrition count, Glycaemic index and Glycaemic load count as a reference value.

16. The apparatus of claim 1, further comprising a notification module operatively coupled to the control unit, wherein the notification unit is configured to generate one or more alerts to the external computing device.

17. The apparatus of claim 16, wherein the one or more alerts comprises at least one of a diet recommendation alert and an alert of the calorie count, the nutrition count, the Glycaemic index and the Glycaemic load count.

18. The apparatus of claim 1, further comprising an illumination device operatively coupled to the stand, wherein the illumination device is configured to provide illumination to the food tray.

\* \* \* \* \*